(12) United States Patent
Massey et al.

(10) Patent No.: US 7,972,841 B2
(45) Date of Patent: Jul. 5, 2011

(54) EXPOSURE DEVICE

(75) Inventors: Elan David Massey, Southampton (GB);
Justine Williamson, Southampton (GB);
Jeremy Francis Neale Phillips,
Southampton (GB)

(73) Assignee: **British American Tobacco
(Investments) Limited**, London (GB)

( * ) Notice: Subject to any disclaimer, the term of this
patent is extended or adjusted under 35
U.S.C. 154(b) by 1291 days.

(21) Appl. No.: 10/515,983

(22) PCT Filed: May 22, 2003

(86) PCT No.: PCT/GB03/02254
§ 371 (c)(1),
(2), (4) Date: Sep. 30, 2005

(87) PCT Pub. No.: WO03/100417
PCT Pub. Date: Dec. 4, 2003

(65) Prior Publication Data
US 2006/0099706 A1    May 11, 2006

(30) Foreign Application Priority Data
May 24, 2002    (GB) .................................. 0211963.4

(51) Int. Cl.
*C12M 3/00*    (2006.01)
(52) U.S. Cl. ............... 435/305.2; 435/286.6; 435/286.7;
435/288.3; 435/288.4; 435/288.5; 435/305.1;
435/305.3; 435/305.4
(58) Field of Classification Search .... 435/288.3–288.5,
435/305.1–305.4, 286.6–287.7
See application file for complete search history.

(56) References Cited

U.S. PATENT DOCUMENTS

| | | | | | |
|---|---|---|---|---|---|
| 4,792,378 | A | * | 12/1988 | Rose et al. | 438/706 |
| 5,602,028 | A | * | 2/1997 | Minchinton | 435/401 |
| 5,627,070 | A | * | 5/1997 | Gruenberg | 435/286.5 |
| 5,795,775 | A | * | 8/1998 | Lahm et al. | 435/297.5 |
| 5,958,762 | A | * | 9/1999 | Stoppini et al. | 435/297.5 |

OTHER PUBLICATIONS

Aufderheide et al. A method for in vitro analysis of the biological activity of complex mixtures such as sidestream cigarette smoke. Exp Toxicol Pathol. vol. 53 No. 2-3. pp. 141-152. (Jun. 2001).*

* cited by examiner

*Primary Examiner* — Michael A Marcheschi
*Assistant Examiner* — Jameson Q Ma
(74) *Attorney, Agent, or Firm* — Charles I. Sherman; Middleton Reutlinger

(57) ABSTRACT

The present invention relates to an exposure device for living cell cultures, the device having a medium chamber common to a plurality of cell culture chambers and medium directing means. The medium chamber, cell culture chambers and the medium directing means may be arranged so as to provide substantially contemporaneous medium exchange at the cell culture chambers.

26 Claims, 2 Drawing Sheets

EXPOSURE DEVICE

CROSS REFERENCE TO PRIOR APPLICATION

Figure 1:
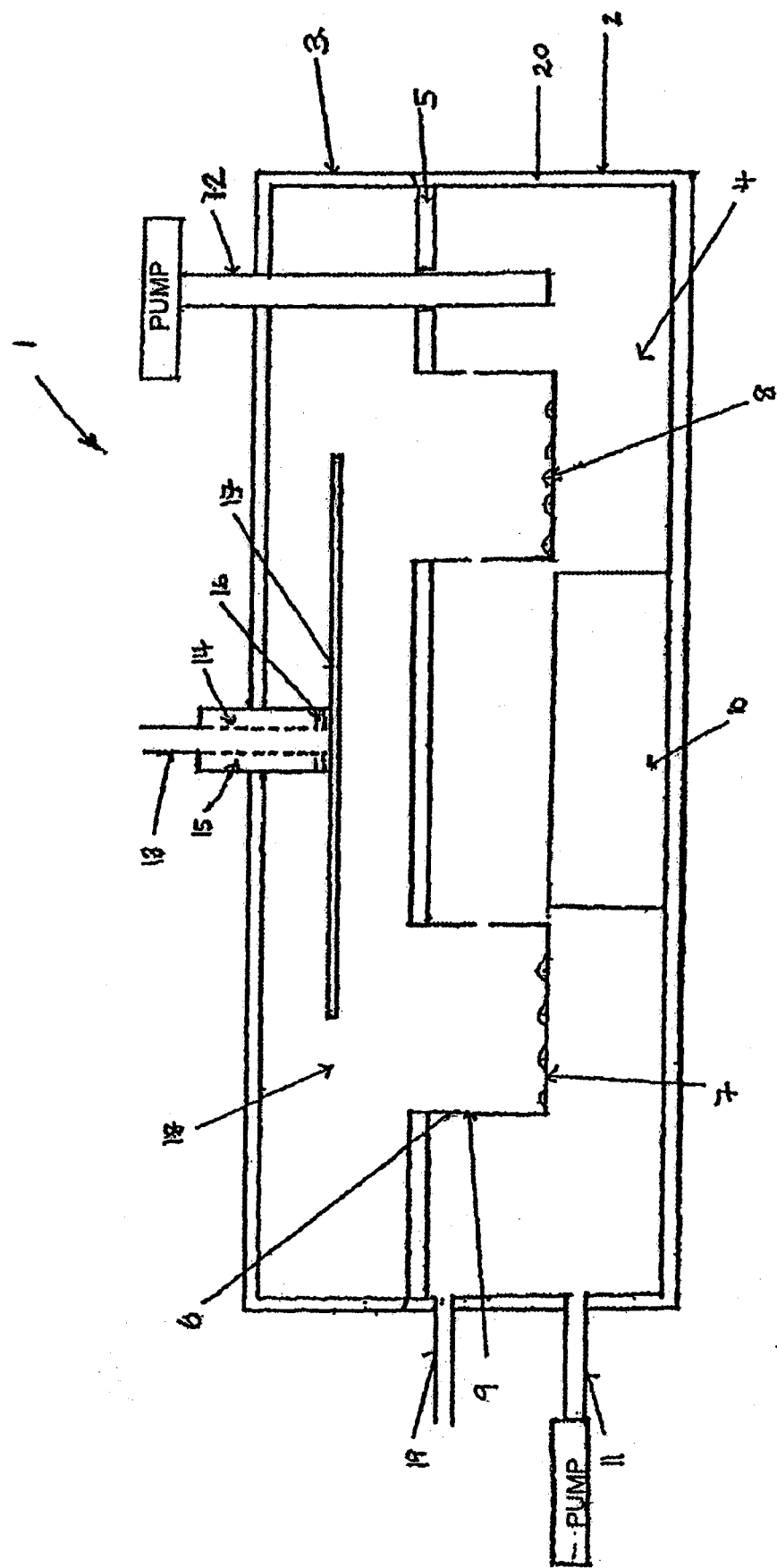

This application is a national stage filing (35 U.S.C. 371) of PCT/GB03/02254, filed on May 22, 2003, which claims priority to and benefit from Great Britain Patent Application No. 0211963.4, filed on May 24, 2002, currently pending.

The present invention relates to an exposure device for fluid mixtures, in particular cigarette smoke and/or gas mixtures, on living cell cultures.

Various exposure devices are known for the delivery of gaseous matter to living cell cultures. Each of the known devices facilitates the delivery of smoke to a cell culture chamber and the delivery of nutrient medium to the base of cell cultures grown in the cell culture chamber. The known devices provide complicated and often costly apparatus designed to prevent mixing of the gaseous matter and the nutrient medium. For example, DE 195 26 533 describes an exposure device in which the gaseous matter is introduced into the top plate of the device and fed by radial smoke distribution means to distinct and separate cell culture chambers. The gaseous matter is then fed away from above the cell culture chambers to a central air outlet in the base plate of the exposure device. The gaseous matter is thus fed directly onto the top surface of the cell cultures. The nutrient medium is supplied to each cell culture chamber through inlet and outlet channels connected to reservoirs in the base plate of the device, each cell culture chamber being located in a separate reservoir, thus keeping the gaseous matter and the nutrient medium separate as well as providing independent medium supply to each of the cell culture chambers. The apparatus described is complicated and costly to manufacture and requires monitoring of the flow rate of the gaseous matter onto the cells in order to ensure the cells are not damaged by the gas flow rate. Additionally a number of medium inlet and outlet pipes are required as each medium reservoir has its own inlet and outlet channel.

In International Patent Application number WO 99/36505 medium is fed through an inlet pipe to a number of separate cell culture chambers. Each cell culture chamber has its own discrete medium chamber thereunder. The apparatus is very complicated and costly to manufacture and does not allow continuous medium exchange at each of the cell culture chambers. The nutrient medium must be removed by the same means that supply the nutrient medium to the cells, thus medium must be removed before fresh medium and/or medium containing additives can be applied to the base of the cell culture.

It is an object of the present invention to provide an exposure device for living cells cultures that has a medium chamber common to all of the cell culture chambers, therefore allowing continuous medium exchange at each of the cell culture chambers.

It is a further object of the present invention to provide an exposure device for living cell cultures that is simple and cheap to manufacture and easy to use.

It is an even further object of the present invention to provide an exposure device for living cultures that is operable to provide either basal or submersion feeding conditions for cells in which the medium supply can be set at selected inlet and outlet flow rates with no further need for human or electronic intervention.

It is a yet further object of the present invention to provide an exposure device for living cell cultures which, in operation, requires no balancing of the medium inlet flow rate and the medium outlet flow rate in order to maintain medium supply to the cell cultures grown therein.

The present invention provides an exposure device for living cell cultures comprising a base portion, a top portion, fluid inlet means, fluid outlet means, medium inlet means, medium outlet means, a medium chamber and a plurality of cell culture chambers, wherein the medium chamber is common to all of the cell culture chambers.

Preferably the medium chamber has medium directing means therewithin. Advantageously the medium directing means is formed from a raised area of the base portion of the exposure device. Suitably the medium directing means is an island within the medium chamber around which the nutrient medium may flow. The medium directing means is positioned within the medium chamber so as to direct the flow of medium under each of the cell culture chambers. Preferably the medium directing means is centrally located within the medium chamber, and is even more preferably located equidistant to each of the cell culture chambers.

Preferably the exposure device comprises two or more cell culture chambers positioned such that the base of each cell culture chamber is located within the medium chamber. Advantageously the exposure device comprises three cell culture chambers. The exposure device may be suitably adapted to comprise any number of cell culture chambers and cell culture chambers of varying sizes. Cell culture chambers suitable for use in the exposure device of the present invention will be readily known to those skilled in the art.

Preferably the base of each of the cell culture chambers is spaced apart from the base of the exposure device by means of a gap to allow the medium to flow freely under each of the cell culture chambers within the medium chamber. Continuous medium exchange at each of the cell culture chambers is facilitated by the free flow of medium under each of the cell culture chambers. Continuous medium exchange is further enhanced by the positioning of the medium directing means.

Suitably the gap through which medium is free to flow between the base of each of the cell culture chambers and the base of the exposure device is at least 1 mm. Preferably the gap between the base of each of the cell culture chambers and the base of the exposure device is about 2 mm or more. Even more preferably the gap between the base of each of the cell culture chambers and the base of the exposure device is about 4 mm.

Medium is supplied to the medium chamber of the exposure device by medium inlet means and is removed from the medium chamber of the exposure device by medium outlet means.

Preferably the medium inlet means is located to supply medium to the base portion of the exposure device whereby medium flows directly into the medium chamber. Even more preferably the medium inlet means is located in a side wall or a bottom wall of the base portion of the exposure device.

Suitably the medium inlet means is a pipe or a tube.

Advantageously the medium outlet means is spaced apart from the medium inlet means and is separated from the medium inlet means by all of the cell culture chambers and/or the medium directing means.

Preferably the medium outlet means is operable to remove medium from the top surface thereof and suitably extends from the top portion of the exposure device into the medium chamber. The position of the intake end of the medium outlet means relative to the base of the cell culture chambers may be adjusted to allow for either basal or submersion feeding of the cell cultures. Alternatively, the medium outlet means may comprise two outlet means, the first positioned to allow for basal feeding of the cell cultures, and the second outlet means being positioned to allow for submersion feeding of the cell cultures.

During basal feeding the medium level is maintained such that medium is always in contact with the base of the cell cultures. In an alternative experimental regime the medium level may be maintained such that the cell cultures are always covered by the medium, such a feeding regime being known in the art as submersion feeding.

Suitably the medium outlet means is a pipe or a tube. Preferably the medium outlet means is a retractable tube which may be locked into the exposure device such that the intake end of the tube is at a height above the base of the device selected by the operator. The height of the intake end of the tube above the base of the exposure device may be equal to the distance of the cell cultures above the base of the device in order to facilitate basal feeding of the cultures or, alternatively, the height of the intake end of the tube above the base of the device may be greater than that of the cell cultures in order to facilitate submersion feeding of the cultures.

Locking of the position of the medium outlet tube may be provided by locking means. The locking means may be a threaded screw arrangement having a central bore, the medium outlet tube passing through the central bore of the threaded screw. Alternatively frictional locking means operable to adjust the position of the medium outlet tube may be provides Preferably the medium outlet means is operably attached to first pump means, the pump means being operable at a controllable first pump rate. Suitably the first pump rate is in the range of about 1 ml/min. and about 20 ml/min. Preferably the first pump rate is about 10 ml/min.

The medium inlet means is suitably operably attached to second pump means, the second pump means being operable at a controllable second pump rate. Suitably the second pump rate is in the range of about 1 ml/min and about 10 ml/min. Preferably the second pump rate is about 7 ml/min.

Advantageously the first pump rate is at least equal to the second pump rate in order that, in operation, the selected medium level is maintained without the need for further intervention. Preferably the first pump rate is greater than the second pump rate. Preferably the first pump rate is greater than the second pump rate and the medium level within the medium chamber does not vary by more than about 3 mm during operation. Preferably the medium level within the medium chamber does not vary by more than about 0.5 mm during operation.

The medium outlet means and/or the medium inlet means may run continuously or, alternatively, may supply/remove nutrient medium in pulses at flow rates selected by the operator. When the medium inlet means is to run continuously, the first pump rate of the medium outlet means is greater than that of the second pump rate of the medium inlet means, therefore no balancing of the pumps is required to maintain the medium at a level set by the operator.

Preferably the medium chamber together with the medium directing means and the medium inlet and outlet means facilitates substantially contemporaneous medium exchange at each of the cell culture chambers. The medium directing means and the cell culture chambers are located with respect to one another so that contemporaneous medium exchange occurs at each of the cell culture chambers.

The exposure device further comprises a fluid exposure chamber common to said cell culture chambers and fluid dispersing means operable to provide substantially contemporaneous fluid exposure to each of the cell culture chambers.

Preferably the fluid inlet means of the present invention is located in the top portion of the exposure device. Even more preferably the fluid inlet means is located in the centre of the top portion of the exposure device.

The fluid inlet means may be adapted to connect with fluid generating means whereby fluid is delivered to the exposure device through the fluid inlet means.

The fluid is passed through the fluid inlet means to the fluid exposure chamber via the fluid dispersing means. Suitably the fluid dispersing means may be a disc-shaped plate above the cell culture chambers operable to disperse the fluid before the fluid reaches the fluid exposure chamber.

Advantageously the fluid flow rate supplied to the cell culture chambers is up to about 700% of available air space per minute.

Preferably the fluid outlet means is located above the level of the medium within the medium chamber such that medium does not flow through the fluid outlet means. More preferably the fluid outlet means is positioned such that the medium outlet means is at a level lower in the medium chamber than the fluid outlet means.

Advantageously the fluid outlet means may be located in a side wall of the base portion of the exposure device or, alternatively, is located in a side wall of the top portion of the exposure device.

Preferably the fluid may be smoke, a gas, an aerosol, or the like, or an air mixture thereof.

Each cell culture chamber is suspended in the medium chamber and is suitably held in position by a cell culture chamber support. Advantageously the cell culture chambers have a fluid passage gap in the side wall thereof. Suitably if a submersion feeding regime is to be used the cell culture chambers may be suitably adapted in order to ensure medium exchange occurs at each of the cell culture chambers. Suitably the cell culture chambers may, for example, comprise a medium passage gap(s). It is much preference that the medium passage gap(s) (if present) are located in a side wall of the cell culture chambers. Cell culture chambers suitable for use in the present invention will be well known to those skilled in the art.

The cell culture chamber support may advantageously be comprised of a sheet of material having a plurality of receiving holes therein into which the cell culture chambers may be lowered. The cell culture chamber support may further act as a partial partition between the fluid exposure chamber and the medium chamber thereby ensuring that the fluid flows through the cell culture chambers before exiting the exposure device through the fluid outlet means.

Preferably the cell culture chamber support is formed from the same material as the exposure device. Preferably the material from which the exposure device and the cell culture chamber support are formed is an inert material. When referred to herein, inert material shall be taken as meaning a material that does not chemically interact with a fluid capable of use in the aforesaid device. Suitably the exposure device and the cell culture chamber support may be formed from a material selected from the group comprising PTFE, Stainless Steel, Poly (Methyl Methacrylate) and Glass. Other suitable materials will be known to those skilled in the art.

The present invention further provides a method of supplying nutrient medium to cell culture chambers whereby nutrient supply means, medium directing means and cell culture chambers are mutually arranged to provide substantially contemporaneous nutrient medium replenishment at each of said cell culture chambers.

The present invention further provides an exposure device for living cell cultures having a medium chamber common to a plurality of cell culture chambers and medium directing means, the cell culture chambers and medium directing means being mutually arranged so as to provide substantially contemporaneous medium exchange at the cell culture chambers.

Figure 2:
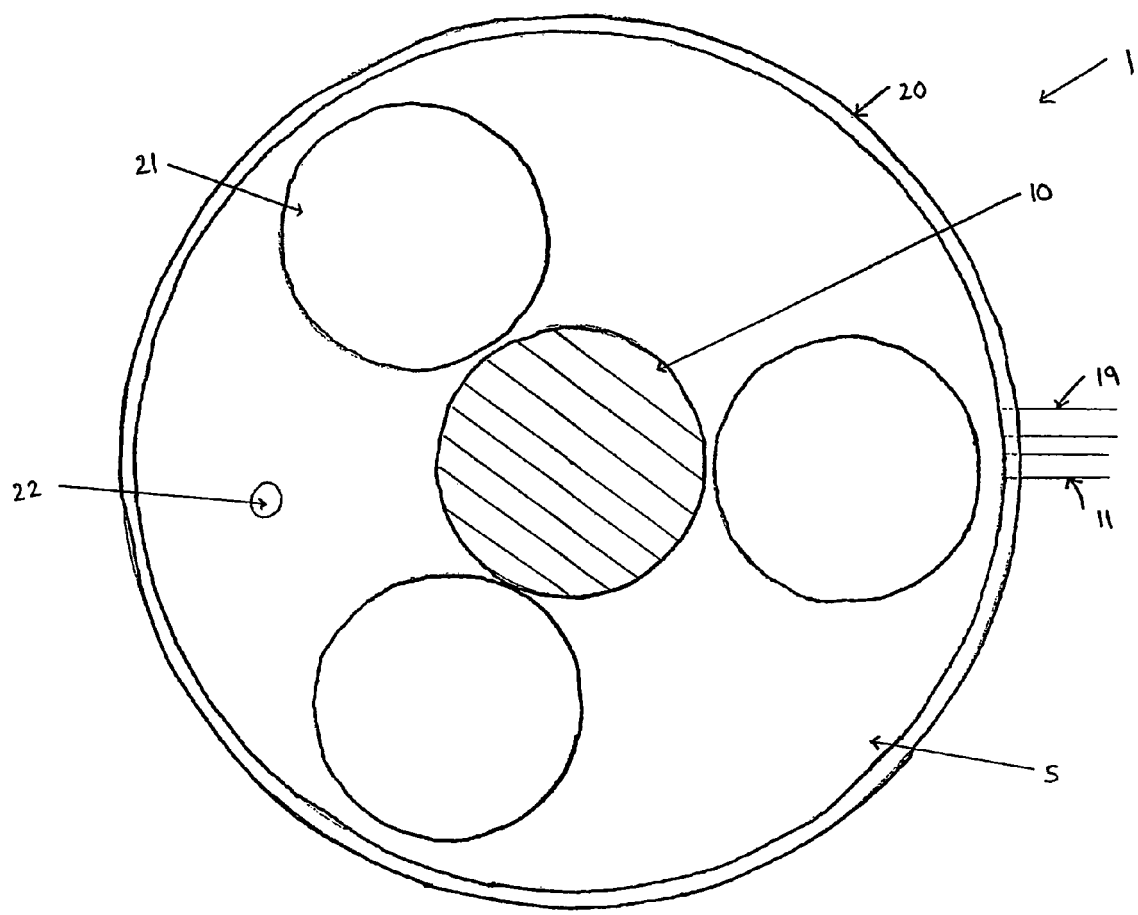

In order that the invention may be easily understood and readily carried into effect, reference will now be made, by way of example, to the following diagrammatic drawings in which:

FIG. 1 shows in longitudinal cross-section an exposure device in accordance with the present invention, and FIG. 2 shows in plan view an exposure device in accordance with one embodiment of the present invention, the top portion of the device, the cell culture chambers and the medium outlet means having been removed.

FIG. 1 of the diagrammatic drawings hereof shows an exposure device 1 in accordance with the present invention. The exposure device comprises a circular base portion 2 and a circular top portion 3 fitted together by means of closure screws (not shown). The top portion 3 and the base portion 2 when closed together form a sealed unit. A rubber seal (not shown) situated between the top portion 3 and the base portion 2 ensures no fluid leakage from the exposure device 1 during the operation thereof. Medium chamber 4 consists of a hollow well for holding nutrient medium and is located in base portion 2 of the exposure device 1. Between the top portion 3 and the base portion 2 is located a cell culture chamber support 5. Cell culture chambers 6 are placed into receiving holes 21 in the cell culture chamber support 5. The base 7 of each cell culture chamber 6 is comprised of a permeable membrane onto which cell cultures 8 may be seeded and grown. Each cell culture chamber 6 may further comprise an insert of inert material (not shown). The insert is preferably a ring of inert material, which ring is placed onto the permeable membrane of the cell culture chamber 6. Cell cultures 8 may be seeded and grown on the permeable membrane with the insert in place. The insert is removed from the cell culture chamber before the cell cultures chambers 6 are placed into the receiving holes 21 in the cell culture chamber support 5. The insert (not shown) prevents growth of cell cultures 8 around the perimeter of the permeable membrane of cell culture chambers 6.

Fluid passage gaps 9 are provided in each cell culture chamber 6 to allow fluid to escape from the cell culture chambers 6. The base 7 of each of the cell culture chambers 6 is spaced apart from the bottom of the exposure device to allow the medium to flow freely under each of the cell culture chambers 6 within the medium chamber 4. Medium directing means 10 is located, in plan view, centrally and equidistant to each of the cell culture chambers 6.

Medium inlet means 11 is located in the base portion 2 and provides medium to the medium chamber 4 by means of a pump. Medium outlet means 12 may be a pipe attached to a second pump for extraction of the nutrient medium from the medium chamber 4. Medium outlet means 12 is removable from the top portion 3 of the exposure device 1. The intake end of medium outlet means 12 passes through a hole 22 in cell culture chamber support 5 into the medium chamber 4. Medium outlet means 12 may be fixed into position by a locking means (not shown). The locking means may be provided by a threaded screw having a central bore therethrough. In this instance, medium outlet means 12 may pass through the central bore of the threaded screw.

Fluid inlet means 13 is centrally located in top portion 3 and comprises an inlet bore 14 through an outer sleeve 15, the inlet bore 14 dispersing fluid through three further radially arranged bores 16 above fluid dispersing means 17 into fluid exposure chamber 18. Fluid outlet means 19 is located in base side wall 20. The fluid outlet means 19 may alternatively be attached to pump means (not shown) for rapid removal of the fluid.

In operation, nutrient medium (not shown) is pumped into the medium chamber 4, the nutrient medium being pre-heated to the required temperature for cell maintenance. The nutrient medium is pumped into the medium chamber 4 at a fixed pumping rate until it either contacts the base of the cell culture chamber 7 as is required for basal feeding of the cell cultures 8, or the medium is allowed to reach a level in the medium chamber 4 at which the cell cultures 8 are submersed in the nutrient medium as is required for submersion feeding of the cell cultures 8.

A pump rate of the medium outlet pump is greater than the pump rate of the medium inlet pump rate, thus ensuring a constant level of nutrient medium in the medium chamber 4. When the nutrient medium contacts the bottom of the medium outlet pipe 12, medium is sucked away by the action of the outlet pump means. The respective pump rates and height of the medium outlet means should be selected to ensure the nutrient medium level deviates by no more than 0.5 mm during operation of the pumps. Once the medium meniscus formed at the intake end of the medium outlet pipe 12 breaks the liquid suction from the outlet pump ceases. The medium level is thereby maintained such that medium always contacts the base 7 of the cell culture chamber 6 during basal feeding or, alternatively always submerges the cell culture 8 to the same depth during submersion feeding thereof. In an alternative arrangement the exposure device 1 is provided with two medium outlet means 12. The intake end of a first medium outlet means 12 is the same distance above the base of the exposure device 1 as the cell cultures 8 and the intake end of a second medium outlet means 12 is a greater distance above the base of the exposure device 1 than the base of the cell cultures 8. Operation of the first medium outlet means 12 allows for basal feeding of the cell cultures 8, and operation of the second medium outlet means 12 allows for submersion feeding of the cell cultures 8.

In a further alternative arrangement (not shown) of medium outlet means 12, there is provided an inverted Y-shaped tube and switching means. The two intake ends of the medium outlet means 12 may be fixed at different distances above the base of the exposure device 1, thus allowing switching between basal and submersion feeding conditions. The switching means may further be provided with timing means to allow switching between basal and submersion feeding conditions at timed intervals.

The nutrient medium is free to flow within the medium chamber 4 such that it flows under the base 7 of each cell culture chamber 6. The medium directing means 10 ensures medium exchange occurs under each cell culture chamber 6 substantially contemporaneously.

In operation, a fluid is piped through the fluid inlet means 13, and is dispersed by the fluid dispersing means 17 and into the fluid exposure chamber 18. The fluid is free to flow over the cell cultures 8. The fluid then disperses out of the cell culture chambers 6 through fluid passage gaps 9 and exits the exposure device 1 through fluid outlet means 19.

In an alternative embodiment of the present invention the fluid outlet means may be located in the top portion of the exposure device. Fluid may disperse throughout the fluid exposure chamber 18 and out through the fluid outlet means 19 having dispersed into the cell culture chambers 6. In this alternative embodiment the cell culture chambers 6 may have solid walls with no fluid passage gaps 9 therein.

The temperature of the nutrient medium may be maintained by placing the exposure device 1 on heating means (not shown). The heating means may suitably be a warming-plate covered with a material capable of heat transfer to prevent hot spots on the base portion 2 of the exposure device 1. The material capable of heat transfer maybe bubble wrap, for example.

In an alternative arrangement (not shown), the temperature of the nutrient medium and the exposure device 1 may be maintained by placing the apparatus inside one or more incubators (not shown). In this arrangement the nutrient medium and the inlet pump means may be located within a first incubator, and at least one exposure device 1 of the present invention may be located within a second incubator. The outlet pump means may be located outwith the second incubator. The first and second incubators may be modified such that the apparatus within the first incubator are operably linked to the apparatus within the second incubator. Furthermore the second incubator may be modified such that the apparatus contained therein are operably linked to the outlet pump means of the present invention. The first and second incubators may be maintained at a temperature suitable for maintenance and growth of the cell cultures 8.

In an alternative embodiment of the present invention, the external perimeter of the exposure device 1 may be of any shape, for example square or rectangular, and the medium directing means is centrally located within the medium chamber and is equidistant to each of the cell culture chambers.

EXAMPLE 1

The exposure device of the present invention may be used in accordance with the following method.

At least two hours before beginning the experiment two large bottles of nutrient medium are pre-warned to a temperature required for cell maintenance and the apparatus are sterilised.

Costar Transwells™ with cultured cells attached to the lower membrane thereof are lowered into the receiving holes in the cell chamber support of the exposure device. The top portion of the exposure device is fitted together with the base portion and closed using the closure screws. The height of the medium outlet pipe above the base of the exposure device is set to facilitate basal and/or submersion feeding conditions and the medium outlet pipe is locked into position using a threaded screw. The medium inlet and outlet pumps are attached and the fluid inlet pipe is attached to a smoking machine.

The exposure device and the medium inlet piping is then wrapped in bubble wrap to ensure full insulation. The device is placed onto a warming-plate set at the required temperature.

The medium outlet pump rate is selected such that it is greater than the medium inlet pump rate and nutrient medium is pumped into the medium chamber of the exposure device to the level determined by the height of the intake end of the medium outlet pipe above the base of the exposure device.

The smoking machine is turned on and the smoke generated from the machine is piped into the fluid exposure chamber, via the fluid inlet pipe, for a set time.

The invention claimed is:

1. An exposure device for living cell cultures comprising a base portion connected with a top portion to form therebetween a nutrient medium chamber adjacent said base portion and a fluid exposure chamber adjacent said top portion which is contiguous and coextensive with said nutrient medium chamber, and a plurality of cell culture chambers extending from said fluid exposure chamber and into said nutrient medium chamber and in a circular array about the center of said fluid exposure chamber;

said nutrient medium chamber being common to all of said cell culture chambers; a fluid inlet for introducing fluid into said fluid exposure chamber; a fluid outlet for removal of fluid from said fluid exposure chamber; a nutrient medium inlet for providing nutrient medium to said nutrient medium chamber;

at least one nutrient medium outlet for extraction of nutrient medium from said nutrient medium chamber;

said nutrient medium chamber being positioned to provide a common well of nutrient medium that passes from said nutrient medium inlet to said at least one nutrient medium outlet; and a passive nutrient medium directing structure consisting of a single island projecting from said base portion and centrally located within said nutrient medium chamber, with a portion of the periphery of said single island adjacent midway between each of said cell culture chambers, in position within the flow of said nutrient medium from said nutrient medium inlet to said at least one nutrient medium outlet and around which said nutrient medium may flow;

said cell culture chambers being in position both to receive nutrient from said common well of nutrient medium in said nutrient medium chamber and to be exposed to said fluid in said fluid exposure chamber as it passes from said fluid inlet to said fluid outlet;

wherein the base of each of said cell culture chambers is spaced apart from the base of said exposure device by a gap such that, in operation, nutrient medium flows freely under each of said cell culture chambers within said nutrient medium chamber.

2. An exposure device according to claim 1, wherein said nutrient medium directing structure is located equidistant to each of said cell culture chambers.

3. An exposure device according to claim 1, wherein said exposure device comprises three cell culture chambers.

4. An exposure device according to claim 1, wherein said gap is at least 1 mm.

5. An exposure device according to claim 1, wherein said gap is about 2 mm or more.

6. An exposure device according to claim 1, wherein said nutrient medium inlet is located in said base portion of said exposure device such that, in operation, nutrient medium flows directly into said nutrient medium chamber.

7. An exposure device according to claim 6, wherein said nutrient medium inlet is located in a side wall of said base portion of said exposure device.

8. An exposure device according to claim 6, wherein said nutrient medium inlet is located in a bottom wall of said base portion of said exposure device.

9. An exposure device according to claim 1, wherein said nutrient medium inlet is a pipe or a tube.

10. An exposure device according to claim 1, wherein said nutrient medium outlet is spaced apart from said nutrient medium inlet.

11. An exposure device according to claim 1, wherein said nutrient medium outlet is spaced apart from said nutrient medium inlet by all of said cell culture chambers and/or said nutrient medium directing means.

12. An exposure device according to claim 1, wherein said nutrient medium outlet extends from the top portion of said exposure device into said nutrient medium chamber.

13. An exposure device according to claim 1, wherein said nutrient medium outlet comprises two outlets.

14. An exposure device according to claim 13, wherein one of said two outlets of said nutrient medium outlet is positioned to allow for basal feeding of cell cultures within said cell culture chambers, and the other of said outlets of said nutrient medium outlet is positioned to allow for submersion feeding of said cell cultures within said cell culture chambers.

15. An exposure device according to claim 1, wherein said nutrient medium outlet is a pipe or a tube.

16. An exposure device according to claim 1, wherein said nutrient medium outlet is operably attached to a first pump and said nutrient medium inlet is operably attached to a second pump.

17. An exposure device according to claim 16, wherein, in operation, said first pump has a controllable first pump rate and said second pump has a controllable second pump rate and said first pump rate is at least equal to said second pump rate.

18. An exposure device according to claim 17, wherein said first pump rate is greater than said second pump rate.

19. An exposure device according to claim 1, wherein said fluid exposure chamber is in flow communication with all said cell culture chambers.

20. An exposure device according to claim 1, wherein said exposure device further comprises fluid dispersing means.

21. An exposure device according to claim 20, wherein said fluid dispersing means is operable to provide substantially contemporaneous fluid exposure to each of said cell culture chambers.

22. An exposure device according to claim 20, wherein said fluid dispersing means is a disc-shaped plate above said cell culture chambers.

23. An exposure device according to claim 1, wherein said fluid inlet is located in said top portion of said exposure device.

24. An exposure device according to claim 1, wherein said fluid inlet is operably connected with fluid generating means whereby fluid is delivered to said exposure device through said fluid inlet.

25. An exposure device according to claim 1, wherein said exposure device further comprises a cell culture chamber support.

26. An exposure device according to claim 1, wherein said exposure device is formed from a material selected from the group consisting of PTFE, Stainless Steel, Poly (Methyl Methacrylate) and Glass.

* * * * *